United States Patent [19]

Rheinheimer et al.

[11] Patent Number: 5,057,143

[45] Date of Patent: Oct. 15, 1991

[54] SALICYLIC ACID DERIVATIVES AND THEIR SULFUR ANALOGS

[75] Inventors: Joachim Rheinheimer, Ludwigshafen; Karl Eicken, Wachenheim; Peter Plath, Frankenthal; Gerhard Paul; Albrecht Harreus, both of Ludwigshafen; Karl-Otto Westphalen, Speyer; Bruno Wuerzer, Otterstadt; Klaus Grossmann, Limburgerhof; Wilhelm Rademacher, Limburgerhof; Johann Jung, Limburgerhof, all of Fed. Rep. of Germany

[73] Assignee: BASF Aktiengesellschaft, Ludwigshafen, Fed. Rep. of Germany

[21] Appl. No.: 366,492

[22] Filed: Jun. 14, 1989

[30] Foreign Application Priority Data

Jun. 16, 1988 [DE] Fed. Rep. of Germany ....... 3820484
Feb. 4, 1989 [DE] Fed. Rep. of Germany ....... 3903365

[51] Int. Cl.$^5$ .................. A01N 43/54; C07D 239/34; C07D 239/52; C07D 239/60

[52] U.S. Cl. ............................................. 71/92; 71/77; 544/300; 544/301; 544/302; 544/310; 544/311; 544/312; 544/314; 544/216; 544/318

[58] Field of Search .................... 71/92; 544/301, 302, 544/311, 312, 314, 316, 318, 300, 310

[56] References Cited

U.S. PATENT DOCUMENTS

| | | | |
|---|---|---|---|
| 4,889,552 | 12/1989 | Wada et al. | 71/92 |
| 4,900,352 | 2/1990 | Wada et al. | 71/92 |
| 4,923,501 | 5/1990 | Saito et al. | 71/92 |
| 4,932,999 | 6/1990 | Saito et al. | 71/92 |
| 4,946,495 | 8/1990 | Wada et al. | 71/92 |
| 4,973,354 | 11/1990 | Hatanaka et al. | 71/92 |
| 4,985,066 | 1/1991 | Wada et al. | 71/92 |
| 4,986,846 | 1/1991 | Gohbara et al. | 71/92 |

FOREIGN PATENT DOCUMENTS

| | | |
|---|---|---|
| 0223406 | 5/1987 | European Pat. Off. . |
| 0249707 | 12/1987 | European Pat. Off. . |
| 0249708 | 12/1987 | European Pat. Off. . |
| 0287072 | 10/1988 | European Pat. Off. . |
| 0287079 | 10/1988 | European Pat. Off. . |
| 315889 | 5/1989 | European Pat. Off. . |
| 336494 | 10/1989 | European Pat. Off. . |

OTHER PUBLICATIONS

Abstract of Japan Patent Disclosure JP-091781, Oct. 25, 1988.

*Primary Examiner*—John M. Ford
*Attorney, Agent, or Firm*—Keil & Weinkauf

[57] ABSTRACT

Salicyclic acid derivatives and their sulfur analogs of the formula I

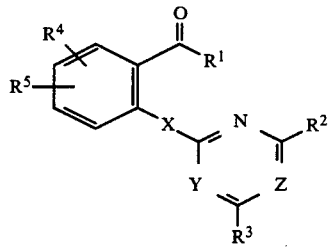

where $R^1$ to $R^5$, X, Y and Z have the meanings given in the disclosure and claims, agents containing the salicyclic acid derivatives, and their use as herbicides.

14 Claims, No Drawings

SALICYLIC ACID DERIVATIVES AND THEIR SULFUR ANALOGS

The present invention relates to salicylic acid derivatives and their sulfur analogs of the formula I

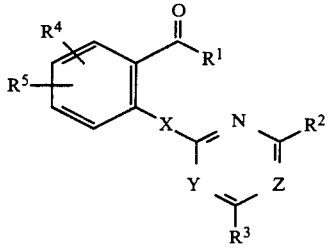

where
$R^1$ is hydrogen;
a succinyliminooxy group;
$C_1$–$C_{10}$-alkoxy which may carry from one to five halogen atoms and carries one of the following substituents: a 5-membered heteroaromatic ring containing from one to three nitrogen atoms, where the aromatic radical in turn may carry from one to four halogen atoms and/or one or two of the following radicals: $C_1$–$C_4$-alkyl, $C_1$–$C_4$-haloalkyl, $C_1$–$C_4$-alkoxy, $C_1$–$C_4$-haloalkoxy and/or $C_1$–$C_4$-alkylthio;
a 5-membered heteroaromatic ring which contains from one to three nitrogen atoms and may carry from one to four halogen atoms and/or one or two of the following radicals: $C_1$–$C_4$-alkyl, $C_1$–$C_4$-haloalkyl, $C_1$–$C_4$-alkoxy, $C_1$–$C_4$-haloalkoxy and/or $C_1$–$C_4$-alkylthio;
a radical —$OR^6$, where
$R^6$ is hydrogen, an alkali metal cation, one equivalent of an alkaline earth metal cation or an organic ammonium ion;
$C_1$–$C_{10}$-alkyl which may carry from one to five halogen atoms and/or one of the following radicals: $C_1$–$C_4$-alkoxy, $C_1$–$C_4$-alkylthio, cyano, $C_1$–$C_8$-alkylcarbonyl, $C_1$–$C_8$-alkoxycarbonyl, phenyl, phenoxy or phenylcarbonyl, where the aromatic radicals in turn may carry from one to five halogen atoms and/or from one to three of the following radicals: $C_1$–$C_4$-alkyl, $C_1$–$C_4$-haloalkyl, $C_1$–$C_4$-alkoxy, $C_1$–$C_4$-haloalkoxy and/or $C_1$–$C_4$-alkylthio, or $C_3$–$C_6$-alkenyl or $C_3$–$C_6$-alkynyl, where these groups in turn may carry from one to five halogen atoms; or
a radical ON=$CR^7R^8$, where
$R^7$ and $R^8$ are each $C_1$–$C_{20}$-alkyl which may carry a phenyl radical or are each phenyl or together form a $C_3$–$C_{12}$-alkylene chain which may carry from one to three $C_1$–$C_3$-alkyl groups;
$R^2$ and $R^3$ are $C_1$–$C_4$-alkyl, $C_1$–$C_4$-haloalkyl, $C_1$–$C_4$-alkoxy, $C_1$–$C_4$-haloalkoxy and/or $C_1$–$C_4$-alkylthio;
X is oxygen or sulfur,
Y and Z are each nitrogen or a methine group =CH—;
$R^4$ is halogen,
a $C_1$–$C_4$-alkyl or $C_1$–$C_4$-alkoxy group which may carry from one to five halogen atoms and/or one of the following groups: $C_1$–$C_4$-alkoxy or $C_1$–$C_4$-alkylthio;
a $C_3$–$C_6$-alkenyl, $C_3$–$C_6$-alkenyloxy, $C_3$–$C_6$-alkynyl or $C_3$–$C_6$-alkynyloxy group which may carry from one to five halogen atoms and/or one of the following radicals: $C_1$–$C_4$-alkoxy or $C_1$–$C_4$-alkylthio;
$C_1$–$C_4$-alkylamino, $C_2$–$C_8$-dialkylamino, arylamino or N-$C_1$–$C_4$-alkyl-N-arylamino;
$R^5$ is hydrogen or one of the radicals $R^4$,
with the proviso that $R^2$ is $C_1$–$C_4$-haloalkyl or X is sulfur or Y is a methine group =C— or $R^4$ is $C_3$–$C_6$-alkenyl, which may carry from one to five halogen atoms, or is $C_3$–$C_6$-haloalkenyloxy when $R^1$ is hydrogen or —$OR^6$, and their environmentally compatible salts.

The present invention furthermore relates to processes for the preparation of compounds I and their use as herbicides and growth regulators of the general formula Ia

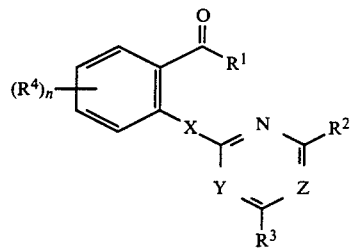

where
$R^1$ is hydrogen;
a succinyliminooxy group;
$C_1$–$C_{10}$-alkoxy which may carry from one to five halogen atoms and carries one of the following substituents: a 5-membered heteroaromatic ring containing from one to three nitrogen atoms, where the aromatic radical in turn may carry from one to four halogen atoms and/or one or two of the following radicals: $C_1$–$C_4$-alkyl, $C_1$–$C_4$-haloalkyl, $C_1$–$C_4$-alkoxy, $C_1$–$C_4$-haloalkoxy and/or $C_1$–$C_4$-alkylthio;
a 5-membered heteroaromatic ring which contains from one to three nitrogen atoms and may carry from one to four halogen atoms and/or one or two of the following radicals: $C_1$–$C_4$-alkyl, $C_1$–$C_4$-haloalkyl and/or one or two of the following radicals: $C_1$–$C_4$-alkyl, $C_1$–$C_4$-haloalkyl, $C_1$–$C_4$-alkoxy, $C_1$–$C_4$-haloalkoxy and/or $C_1$–$C_4$-alkylthio;
a radical —$OR^6$, where
$R^6$ is hydrogen, an alkali metal cation, one equivalent of an alkaline earth metal cation or an organic ammonium ion;
$C_1$–$C_{10}$-alkyl which may carry from one to five halogen atoms and/or one of the following radicals: $C_1$–$C_4$-alkoxy, $C_1$–$C_4$-alkylthio, cyano, $C_1$–$C_8$-alkylcarbonyl, $C_1$–$C_8$-alkoxycarbonyl, phenyl, phenoxy or phenylcarbonyl, where the aromatic radical in turn may carry from one to five halogen atoms and/or from one to three of the following radicals: $C_1$–$C_4$-alkyl, $C_1$–$C_4$-haloalkyl, $C_1$–$C_4$-alkoxy, $C_1$–$C_4$-haloalkoxy and/or $C_1$–$C_4$-alkylthio, or $C_3$–$C_6$-alkenyl or $C_3$–$C_6$-alkynyl, where these groups in turn may carry from one to five halogen atoms; or
a radical ON=$CR^7R^8$, where
$R^7$ and $R^8$ are each $C_1$–$C_{20}$-alkyl which may carry a phenyl radical or are each phenyl or together form a $C_3$–$C_{12}$-alkylene chain which may carry from one to three $C_1$–$C_3$-alkyl groups;

$R^2$ and $R^3$ are $C_1$-$C_4$-alkyl, $C_1$-$C_4$-haloalkyl, $C_1$-$C_4$-alkoxy, $C_1$-$C_4$-haloalkoxy and/or $C_1$-$C_4$-alkylthio;

X is oxygen;

Y is nitrogen;

Z is nitrogen or a methine group =CH—;

$R^4$ is halogen, a $C_1$-$C_4$-alkyl or $C_1$-$C_4$-alkoxy group which may carry from one to five halogen atoms and/or one of the following groups: $C_1$-$C_4$-alkoxy or $C_1$-$C_4$-alkylthio;

a $C_3$-$C_6$-alkenyl, $C_3$-$C_6$-alkenyloxy, $C_3$-$C_6$-alkynyl or $C_3$-$C_6$-alkynyloxy group which may carry from one to five halogen atoms and/or one of the following radicals: $C_1$-$C_4$-alkoxy or $C_1$-$C_4$-alkylthio; $C_1$-$C_4$-alkylamino, $C_2$-$C_8$-dialkylamino, arylamino or $N$-$C_1$-$C_4$-alkyl-$N$-arylamino, and n is 0, 1 or 2.

The literature (EP-A 223 406, EP-A 249 707, EP-A 249 708, EP-A 287 072 and EP-A 287 079) describes herbicidal substituted salicylic acids and their sulfur analogs. However, their action is unsatisfactory.

It is an object of the present invention to provide novel salicylic acid derivatives or their sulfur analogs having improved herbicidal properties and having plant growth-regulating properties.

We have found that this object is achieved by the compounds of the formula I which are defined at the outset. We have also found processes for the preparation of the compounds I and methods for controlling undesirable plant growth with the compounds I. We have furthermore found that salicylic acid derivatives of the general formula Ia defined above have excellent plant growth-regulating properties.

Compounds of the formula I are obtained, for example, by reacting a correspondingly substituted benzoic acid derivative of the formula II, which is known or can be prepared by a conventional method starting from known intermediates, with a corresponding compound of the formula III in the presence of a base.

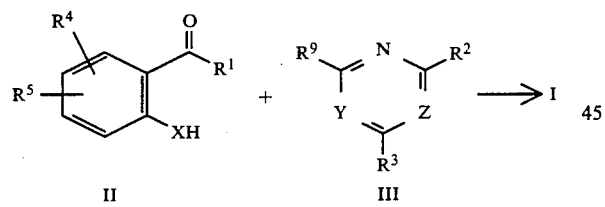

In formula III, $R^9$ is halogen, such as chlorine, bromine or iodine, arylsulfonyl or alkylsulfonyl, such as toluenesulfonyl or methylsulfonyl, or another equivalent leaving group. Compounds of the formula III having a reactive substituent $R^9$ are known or are readily obtainable with the general technical knowledge. Suitable bases are alkali metal or alkaline earth metal hydrides, such as NaH and $CaH_2$, alkali metal hydroxides, such as NaOH and KOH, alkali metal carbonates, such as $Na_2CO_3$ and $K_2CO_3$, alkali metal amides, such as $NaNH_2$ and lithium diisopropylamide, and tertiary amines. When an inorganic base is used, a phase transfer catalyst can be added if this promotes the reaction.

Where the compounds of the formula I prepared in the manner described are carboxylic acids (i.e. when $R^1$ is hydroxyl), other compounds described can, for example, also be prepared from them by first converting the carboxylic acid in a conventional manner into an activated form, such as a halide or imidazolide, and then reacting this with the corresponding hydroxyl compound. These two steps can furthermore be simplified, for example, by allowing the carboxylic acid to act on the hydroxyl compound in the presence of a water-eliminating agent, such as a carbodiimide.

Because of the herbicidal activity, compounds I in which the substituents have the following meanings are preferred:

$R^1$ is hydrogen or succinyliminooxy, alkoxy, in particular methoxy, ethoxy, propoxy, 1-methylethoxy, butoxy, 1-methylpropoxy, 2-methylpropoxy, 1,1-dimethylethoxy, n-pentyloxy, 1-methylbutoxy, 2-methylbutoxy, 3-methylbutoxy, 1,2-dimethylpropoxy, 1,1-dimethylpropoxy, 2,2-dimethylpropoxy, 1-ethylpropoxy, n-hexyloxy, 1-methylpentyloxy, 2-methylpentyloxy, 3-methylpentyloxy, 4-methylpentyloxy, 1,2-dimethylbutoxy, 1,3-dimethylbutoxy, 2,3-dimethylbutoxy, 1,1-dimethylbutoxy, 2,2-dimethylbutoxy, 3,3-dimethylbutoxy, 1,1,2-trimethylpropoxy, 1,2,2-trimethylpropoxy, 1-ethylbutoxy, 2-ethylbutoxy, 1-ethyl-2-methylpropoxy, n-heptyloxy, 1-methylhexyloxy, 2-methylhexyloxy, 3-methylhexyloxy, 4-methylhexyloxy, 5-methylhexyloxy, 1-ethylpentyloxy, 2-ethylpentyloxy, 1-propylbutoxy or octyloxy, which may carry from one to five halogen atoms, such as fluorine, chlorine, bromine or iodine, in particular fluorine, chlorine or bromine, and additionally carries one of the following substituents:

5-membered hetaryl, such as pyrrolyl, pyrazolyl, imidazolyl or triazolyl, in particularly imidazolyl or pyrazolyl, where the aromatic radical is bonded via nitrogen and in turn can carry from one to four halogen atoms as stated above, in particular fluorine or chlorine, and/or one or two of the following radicals: alkyl, such as methyl, ethyl, propyl, 1-methylethyl, butyl, 1-methylpropyl, 2-methylpropyl or 1,1-dimethylethyl, preferably methyl, ethyl or 1-methylethyl, haloalkyl, such as fluoromethyl, difluoromethyl, trifluoromethyl, chlorodifluoromethyl, dichlorofluoromethyl, trichloromethyl, 1-fluoroethyl, 2-fluoroethyl, 2,2-difluoroethyl, 2,2,2-trifluoroethyl, 2-chloro-2,2-difluoroethyl, 2,2-dichloro-2-fluoroethyl, 2,2,2-trichloroethyl or pentafluoroethyl, in particular difluoromethyl, trifluoromethyl, 2,2,2-trifluoroethyl or pentafluoroethyl; alkoxy as stated above, having from one to four carbon atoms, haloalkoxy, such as difluoromethoxy, trifluoromethoxy, chlorodifluoromethoxy, dichlorofluoromethoxy, 1-fluoroethoxy, 2-fluoroethoxy, 2,2-difluoroethoxy, 1,1,2,2-tetrafluoroethoxy, 2,2,2-trifluoroethoxy, 2-chloro-1,1,2-trifluoroethoxy or pentafluoroethoxy, in particular trifluoroethoxy, and/or alkylthio, such as methylthio, ethylthio, propylthio, 1-methylethylthio, butylthio, 1-methylpropylthio, 2-methylpropylthio or 1,1-dimethylethylthio, in particular methylthio or ethylthio;

5-membered hetaryl as stated above, in particular imidazolyl, pyrazolyl or triazolyl, which in general and in particular may carry the abovementioned halogen atoms, alkyl groups, haloalkyl groups, alkoxy groups, haloalkoxy groups and/or alkylthio groups; a radical $OR^6$, where $R^6$ is hydrogen, a cation of an alkali metal or a cation of an alkaline earth metal, such as lithium, sodium, potassium, calcium, magnesium or barium, or an environmentally compatible organic ammonium ion; alkyl, in particular methyl, ethyl, propyl, 1- methylethyl, butyl, 1-methylpropyl, 2-methylpropyl, 1,1-dimethylethyl, n-pentyl, 1-methylbutyl, 2-methylbutyl, 3-methylbutyl, 1,2-dimethylpropyl, 1,1-dimethylpropyl, 2,2-dimethylpropyl, 1-ethylpropyl, n-hexyl, 1-methylpentyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl, n-heptyl, 1-methylhexyl, 2-methylhexyl, 3-methylhexyl, 4-methylhexyl, 5-methylhexyl, 1-ethylpentyl, 2-ethylpentyl, 1-propylbutyl or octyl which may carry from one to five of the abovementioned halogen atoms, in particular fluorine and chlorine, and/or one of the following radicals: cyano, alkoxy or alkylthio of one to four carbon atoms, as stated above, in particular methoxy, ethoxy, 1-methylethoxy or methylthio;

alkylcarbonyl, in particular methylcarbonyl, ethylcarbonyl, propylcarbonyl, 1-methylethylcarbonyl, butylcarbonyl, 1-methylpropylcarbonyl, 2-methylpropylcarbonyl, 1,1-dimethylethylcarbonyl, pentylcarbonyl, 1-methylbutylcarbonyl, 2-methylbutylcarbonyl, 3-methylbutylcarbonyl, 1,1-dimethylpropylcarbonyl, 1,2-dimethylpropylcarbonyl, 2,2-dimethylpropylcarbonyl, 1-ethylpropylcarbonyl, hexylcarbonyl, 1-methylpentylcarbonyl, 2-methylpentylcarbonyl, 3-methylpentylcarbonyl, 4-methylpentylcarbonyl, 1,1-dimethylbutylcarbonyl, 1,2-dimethylbutylcarbonyl, 1,3-dimethylbutylcarbonyl, 2,2-dimethylbutylcarbonyl, 2,3-dimethylbutylcarbonyl, 3,3-dimethylbutylcarbonyl, 1-ethylbutylcarbonyl, 2-ethylbutylcarbonyl, 1,1,2-trimethylpropylcarbonyl, 1,2,2-trimethylpropylcarbonyl, 1-ethyl-1-methylpropylcarbonyl and 1-ethyl-2-methylpropylcarbonyl; alkoxycarbonyl, such as methoxycarbonyl, ethoxycarbonyl, propoxycarbonyl, 1-methylethoxycarbonyl, butoxycarbonyl, 1-methylpropoxycarbonyl, 2-methylpropoxycarbonyl, 1,1-dimethylethoxycarbonyl, n-pentyloxycarbonyl, 1-methylbutoxycarbonyl, 2-methylbutoxycarbonyl, 3-methylbutoxycarbonyl, 1,2-dimethylpropoxycarbonyl, 1,1-dimethylpropoxycarbonyl, 2,2-dimethylpropoxycarbonyl, 1-ethylpropoxycarbonyl, n-hexyloxycarbonyl, 1-methylpentyloxycarbonyl, 2-methylpentyloxycarbonyl, 3-methylpentyloxycarbonyl, 4-methylpentyloxycarbonyl, 1,2-dimethylbutoxycarbonyl, 1,3-dimethylbutoxycarbonyl, 2,3-dimethylbutoxycarbonyl, 1,1-dimethylbutoxycarbonyl, 2,2-dimethylbutoxycarbonyl, 3,3-dimethylbutoxycarbonyl, 1,1,2-trimethylpropoxycarbonyl, 1,2,2-trimethylpropoxycarbonyl, 1-ethylbutoxycarbonyl, 2-ethylbutoxycarbonyl, 1-ethyl-2-methylpropoxycarbonyl, n-heptyloxycarbonyl, 1-methylhexyloxycarbonyl, 2-methylhexyloxycarbonyl, 3-methylhexyloxycarbonyl, 4-methylhexyloxycarbonyl, 5-methylhexyoxycarbonyl, 1-ethylpentyloxycarbonyl, 2-ethylpentyloxycarbonyl, 1-propylbutoxycarbonyl or octyloxycarbonyl, in particular methoxycarbonyl, ethoxycarbonyl, 1-methylethoxycarbonyl or 1-methylpropoxycarbonyl;

phenyl, phenoxy or phenylcarbonyl, where these aromatic radicals may in turn carry from one to five halogen atoms as stated above, in particular fluorine, chlorine or bromine, and/or from one to three of the following radicals: alkyl, haloalkyl, alkoxy, haloalkoxy and/or alkylthio, each of one to four carbon atoms, as stated in general and in particular above, or alkenyl, such as 2-propenyl, 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-2-butenyl, 1,2-dimethyl-3-butenyl, 1,3-dimethyl-2-butenyl, 1,3-dimethyl-3-butenyl, 2,2-dimethyl-3-butenyl, 2,3-dimethyl-2-butenyl, 2,3-dimethyl-3-butenyl, 1-ethyl-2-butenyl, 1-ethyl-3-butenyl, 2-ethyl-2-butenyl, 2-ethyl-3-butenyl, 1,1,2-trimethyl-2-propenyl, 1-ethyl-1-methyl-2-propenyl or 1-ethyl-2-methyl-2-propenyl, in particular 2-propenyl, 2-butenyl, 3-methyl-2-butenyl or 3-methyl-2-pentenyl; alkynyl, such as 2-propynyl, 2-butynyl, 3-butynyl, 1-methyl-2-propynyl, 2-pentynyl, 3-pentynyl, 4-pentynyl, 1-methyl-3-butynyl, 2-methyl-3-butynyl, 1-methyl-2-butynyl, 1,1-dimethyl-2-propynyl, 1-ethyl-2-propynyl, 2-hexynyl, 3-hexynyl, 4-alkynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 1-ethyl-2-butynyl, 1-ethyl-3-butynyl, 2-ethyl-3-butynyl or 1-ethyl-1-methyl-2-propynyl, preferably 2-propynyl, 2-butynyl, 1-methyl-2-propynyl or 1-methyl-2-butynyl, in particular 2-propynyl, where these alkenyl and alkynyl groups can carry from one to five of the halogen atoms stated above in general and in particular;

a radical $ON=CR^7R^8$, where $R^7$ and $R^8$ are each straight-chain or branched $C_1$-$C_{20}$-alkyl, preferably $C_1$-$C_{15}$-alkyl, in particular $C_1$-$C_9$-alkyl, which may carry a phenyl radical, or are each phenyl or together form $C_3$-$C_{12}$-alkylene, preferably $C_4$-$C_7$-alkylene, which may carry from one to three $C_1$-$C_3$-alkylene groups, preferably methyl or ethyl;

$R^2$ and $R^3$ each in general and in particular the alkyl, haloalkyl, alkoxy, haloalkoxy and/or alkylthio groups stated for $R^1$, each of one to four carbon atoms;

X is oxygen or sulfur;

Y and Z are each nitrogen or a methine group $=CH-$;

$R^4$ is halogen as stated for $R^1$, in particular fluorine, chlorine or bromine;

alkyl or alkoxy, each of one to four, in particular one to three, carbon atoms, which may be monosubstituted to pentasubstituted by halogen, in particular fluorine or chlorine, and/or monosubstituted by alkoxy or alkylthio, each of one to four, in particular one or two, carbon atoms;

alkenyl, alkenyloxy, alkynyl or alkynyloxy, each of three to six, in particular three to five, carbon atoms, which may be monosubstituted to pentasubstituted by halogen, in particular fluorine or chlorine, and/or monosubstituted by alkoxy or alkylthio, each of one to four, in particular one or two, carbon atoms;

alkylamino, such as methylamino, ethylamino, propylamino, 1-methylethylamino, butylamino, 1-methylpropylamino, 2-methylpropylamino or 1,1- dimethylethylamino, in particular methylamino or 1,1-dimethylethylamino; dialkylamino, such as dimethylamino, diethylamino, dipropylamino, di-1-methylethylamino, dibutylamino, di-1-methylpropylamino, di-2-methylpropylamino, di-1,1-dimethylamino, ethylmethylamino, propylmethylamino, 1-methylethylmethylamino, butylmethylamino, 1-methylpropylmethylamino, 2-methylpropylmethylamino, 1,1-dimethylethylmethylamino, propylethylamino, 1-methylethylethylamino, butylethylamino, 1-methylpropylethylamino, 2-methylpropylethylamino, 1,1-dimethylethylethylamino, 1-methylethylpropylamino, butylpropylamino, 1-methylpropylpropylamino, 2-methylpropylpropylamino, 1,1-dimethylethylpropylamino, 1-methylethylbutylamino, 1-methylpropylbutylamino, 2-methylpropylbutylamino or 1,1-dimethylethylbutylamino, in particular dimethylamino, diethylamino or di-1-methylethylamino;

arylamino, such as phenylamino, or N-alkylarylamino, such as N-methylphenylamino, N-ethylphenylamino, N-propylphenylamino, N-1-methylethylphenylamino, N-butylphenylamino, N-1-methylpropylphenylamino, N-2-methylpropylphenylamino or N-1,1-dimethylethylphenylamino, in particular N-methylphenylamino or N-1,1-dimethylethylphenylamino, and $R^5$ is hydrogen or in general and in particular one of the radicals $R^4$, and their environmentally compatible salts, with the proviso that $R^2$ is $C_1$–$C_4$-haloalkyl or X is sulfur or Y is a methine group =CH— or $R^4$ is $C_3$–$C_6$-alkenyl, which may carry from one to five halogen atoms, or is $C_3$–$C_6$-haloalkenyloxy.

Particularly preferred herbicidal active ingredients are compounds of the formula I, in which
$R^1$ is ON=$CR^7R^8$,
and those in which
$R^1$ is an unsubstituted or substituted 5-membered heterocyclic structure,
and those in which
X is sulfur,
Y is nitrogen and
Z is a methine group.

Because of the plant growth-regulating action, preferred compounds Ia are those in which the substituents have the following meanings:

$R^1$ is hydrogen, hydroxyl,
$C_1$–$C_{15}$-alkoxy, in particular $C_1$–$C_{10}$-alkoxy, e.g. methoxy, ethoxy, propoxy, butoxy, pentyloxy or hexyloxy, which is unsubstituted or substituted by $C_1$–$C_3$-alkylthio, $C_1$–$C_3$-alkoxy, phenoxy, $C_1$–$C_4$-alkylcarbonyl or phenylcarbonyl, phenyl-$C_1$–$C_3$-alkoxy which is unsubstituted or monosubstituted to trisubstituted in the phenyl moiety by halogen, such as fluorine, bromine or iodine, methoxy or methyl, low molecular weight alkenyloxy, for example $C_2$–$C_{10}$-alkenyloxy, in particular $C_2$–$C_6$-alkenyloxy, which is unsubstituted or substituted by $C_1$–$C_3$-alkyl or halogen, in particular chlorine or bromine, low molecular weight alkynyloxy, for example $C_2$–$C_4$-alkynyloxy, in particular propargyloxy, which is unsubstituted or substituted by $C_1$–$C_3$-alkyl, $C_3$–$C_{10}$-alkoxycarbonylalkoxy, in particular $C_3$–$C_7$-alkoxycarbonylalkoxy, e.g. methoxycarbonylmethoxy, ethoxycarbonylmethoxy, n-propoxycarbonylmethoxy, methoxycarbonylethoxy, ethoxycarbonylethoxy or ethoxycarbonylpropoxy, 5-membered hetaryl, in particular imidazolyl, pyrazolyl or 1,2,3- or 1,2,4-pyrazolyl, a radical ON=$CR^7R^8$ (alkylideneaminoxy) which is derived from symmetric or asymmetric, branched or straight-chain $C_3$–$C_{20}$-, preferably $C_3$–$C_{15}$-, particularly preferably $C_3$–$C_{11}$-(alkyl ketones) or $C_8$–$C_{18}$-, preferably $C_8$–$C_{13}$-(alkylphenyl ketones), $C_4$–$C_{12}$-, preferably $C_5$–$C_8$-cycloalkylideneaminooxy which is unsubstituted or monosubstituted to trisubstituted by methyl, $R^2$ and $R^3$ are each low molecular weight alkyl, for example $C_1$–$C_6$-alkyl, low molecular weight haloalkyl, for example of 1 to 6, in particular 1 to 4, carbon atoms and 1 to 4 halogen atoms, such as fluorine, chlorine or bromine, $C_1$- or $C_2$-chloro and fluoroalkyl, e.g. trifluoromethyl and difluoromethyl, being preferred, low molecular weight alkoxy and alkylthio, such as $C_1$–$C_3$-alkoxy and $C_1$–$C_3$-alkylthio, or low molecular weight haloalkoxy, the abovementioned haloalkyl radicals being preferred, X is oxygen,
Y is nitrogen,
Z is nitrogen or the methine group =CH—,
$R^4$ is hydrogen,
halogen, such as fluorine, chlorine, bromine or iodine, alkyl, such as branched or straight-chain $C_1$–$C_6$-alkyl, low molecular weight haloalkyl as stated for $R^2$ and $R^3$, alkenyl, for example $C_2$–$C_6$-alkenyl, in particular $C_2$–$C_4$-alkenyl, which is unsubstituted or substituted by $C_1$–$C_3$-alkyl or halogen, such as chlorine or fluorine, low molecular weight alkoxy, for example $C_1$–$C_6$-alkoxy, in particular $C_1$–$C_4$-alkoxy, $C_3$–$C_6$-alkenyloxy which is unsubstituted or substituted by $C_1$–$C_3$-alkyl or halogen, such as fluorine, chlorine or bromine, or $C_2$–$C_4$-alkynyloxy, such as propargyloxy, and
n is 0, 1 or 2.

Depending on the stated number of carbon atoms, alkyl, or alkyl in an alkoxy group, is methyl, ethyl, propyl, isopropyl, butyl, sec-butyl, tert-butyl, pentyl and its isomers, hexyl and its isomers, heptyl and its isomers or octyl and its isomers. In the case of the higher homologs, the isomers are also included in each case. Cycloalkyl in the cycloalkylideneamino group is, for example, cyclobutyl, cyclopentyl, cyclohexyl, cycloheptyl or cyclooctyl. Alkenyl, or alkenyl in an alkenyloxy group, is, for example, allyl, propenyl, butenyl, but-2-yl, pentenyl, hexenyl or heptenyl.

Of the abovementioned compounds some are particularly noteworthy, i.e. those in which $R^1$ is hydroxyl, unsubstituted or $C_1$- or $C_2$-alkoxy-substituted or $C_1$- or $C_2$-alkylthio-substituted $C_1$–$C_5$-alkoxy, benzyloxy or $C_2$–$C_5$-alkenyloxy which is unsubstitued or substituted by methyl or chlorine, or $R^1$ is propargyloxy, or is alkylideneaminooxy which is derived from a branched or straight-chain $C_3$–$C_{11}$-(alkyl ketone), or $R^1$ is $C_5$–$C_8$-cycloalkylideneaminooxy or imidazolyl, $R^2$ and $R^3$ are each trifluoromethyl, $C_1$–$C_3$-alkoxy, difluoromethoxy or $C_1$–$C_3$-alkylthio, Z is nitrogen or the methine group, and $R^4$ is hydrogen, fluorine, chlorine, bromine, $C_1$–$C_4$-alkyl, allyl, methylallyl, chloroallyl, $C_1$- or $C_2$-alkoxy, allyloxy, methylallyloxy or chloroallyloxy.

Suitable salts of the compounds of the formula Ia are agriculturally usable salts, for example alkali metal salts, in particular the potassium or sodium salt, alkaline earth metal salts, in particular the calcium, magnesium or barium salt, and manganese, copper, zinc or iron salts and ammonium, phosphonium, sulfonium or sulfoxonium salts, for example ammonium salts, tetralkylammonium salts, benzyltrialkylammonium salts, trialkylsulfonium salts or trialkylsulfoxonium salts.

The novel herbicidal and growth-regulating agents I and Ia, or agents containing them, may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as N,N-dimethylformamide, dimethyl sulfoxide, N-methylpyrrolidone, water, etc. are suitable.

Aqueous formulations may be prepared from emulsion concentrates, pastes, dispersions, wettable powders or water-dispersible granules by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctyl phenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90, % by weight of active ingredient. The active ingredients are employed in a purity of from 90 to 100, preferably from 95 to 100, % (according to the NMR spectrum).

The compounds I or Ia according to the invention may be formulated for instance as follows:

I. 90 parts by weight of compound no. 1.001 is mixed with 10 parts by weight of N-methyl-alpha-pyrrolidone. A mixture is obtained which is suitable for application in the form of very fine drops.

II. 20 parts by weight of compound no. 1.008 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzene-sulfonic acid, and 5 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

III. 20 parts by weight of compound no. 1.011 is dissolved in a mixture consisting of 40 parts by weight of cyclohexanone, 30 parts by weight of isobutanol, 20 parts by weight of the adduct of 7 moles of ethylene oxide and 1 mole of isooctylphenol, and 10 parts by weight of the adduct of 40 moles of ethylene oxide and 1 mole of castor oil. By pouring the solution into 100,000 parts by weight of water and finely distributing it therein, an aqueous dispersion is obtained containing 0.02% by weight of the active ingredient.

IV. 20 parts by weight of compound no. 1.047 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

V. 20 parts by weight of compound no. 1.022 is well mixed with 3 parts by weight of the sodium salt of diisobutylnaphthalene-alpha-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

VI. 3 parts by weight of compound no. 1.014 is intimately mixed with 97 parts by weight of particulate kaolin. A dust is obtained containing 3% by weight of the active ingredient.

VII. 30 parts by weight of compound no. 1.010 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 20 parts by weight of compound no. 1.008 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

IX. 90 parts by weight of compound no. 2.018 is mixed with 10 parts by weight of N-methyl-alpha-pyrrolidone. A mixture is obtained which is suitable for application in the form of very fine drops.

X. 20 parts by weight of compound no. 2.043 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

XI. 20 parts by weight of compound no. 2.013 is dissolved in a mixture consisting of 40 parts by weight of cyclohexanone, 30 parts by weight of isobutanol, 20 parts by weight of the adduct of 7 moles of ethylene oxide and 1 mole of isooctylphenol, and 10 parts by weight of the adduct of 40 moles of ethylene oxide and 1 mole of castor oil. By pouring the solution into 100,000 parts by weight of water and finely distributing it therein, an aqueous dispersion is obtained containing 0.02% by weight of the active ingredient.

XII. 20 parts by weight of compound no. 2.009 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

XIII. 20 parts by weight of compound no. 2.009 is well mixed with 3 parts by weight of the sodium salt of diisobutylnaphthalene-alpha-sulfonic acid, 17 parts by weight of the sodium salt of a lignin-sulfonic acid obtained from a sulfite waste liquor, and 60 parts by weight of powedered silica gel, and triturated in a hammer mill. By uniformly distributing the mixture in 20,000 parts by weight of water, a spray liquor is obtained containing 0.1% by weight of the active ingredient.

XIV. 3 parts by weight of compound no. 2.013 is intimately mixed with 97 parts by weight of particulate kaolin. A dust is obtained containing 3% by weight of the active ingredient.

XV. 30 parts by weight of compound no. 2.012 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

XVI. 20 parts by weight of compound no. 2.014 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The herbicidal or growth-regulating active ingredients, or agents containing them, may be applied pre-or postemergence. If certain crop plants tolerate the active ingredients less well, application techniques may be used in which the herbicidal agents are sprayed from suitable equipment in such a manner that the leaves of sensitive crop plants are if possible not touched, and the agents reach the soil or the unwanted plants growing beneath the crop plants (post-directed, lay-by treatment).

The application rates for the herbicidal use of the active ingredients depend on the objective to be achieved, the time of the year, the plants to be combated and their growth stage, and are from 0.001 to 3.0, preferably 0.005 to 0.5, kg of active ingredient per hectare.

The salicylic acid derivatives of the formula Ia may exercise a variety of influences on practically all plant development stages, and are therefore used as growth regulators. The diversity of action of growth regulators depends especially on a) the type and variety of plant;

b) the time applied, with reference to the development stage of the plants and the time of the year;

c) the place and method of application (seed treatment, soil treatment, or application to foliage);

d) climatic factors, e.g., average temperature, amount of precipitate, sunshine and duration;

e) soil conditions (including fertilization);

f) the formulation of the active ingredient; and g) the concentration at which the active ingredient is applied.

A description of some of the various possibilities of using the growth regulators according to the invention in agriculture and horticulture is given below.

A. Vegetative plant growth can be inhibited to a considerable extent, a fact which is manifested particularly in a reduction in plant height. The treated plants thus have a compact habit; furthermore, the leaf color is darker.

Of advantage in practice is for example the reduction in grass growth on roadsides, hedges, canal embankments and on areas such as parks, sportsgrounds, fruit orchards, lawns and airfields, thus reducing expensive and time-consuming mowing.

A further feature of economic interest is the increase in the rigor of crops which tend to lodge, such as cereals, Indian corn, sunflowers and soybeans. The shortening and strengthening of the stem thus caused reduces or eliminates the danger of lodging under unfavorable weather conditions.

The use of growth regulators is also important for inhibiting plant height and changing the time of ripening in cotton. It is thus possible for this important crop to be harvested completely mechanically.

Pruning costs can be saved in fruit and other trees. Furthermore, growth regulators can break up the alternate bearing of fruit trees.

Growth regulators may also increase or inhibit lateral branching. This is of interest when, for instance in tobacco plants, it is desired to inhibit the formation of lateral shoots (suckers) in favor of leaf development.

With the growth-regulating compounds I, it is possible for instance in winter rape to considerably increase the resistance to freeze injury. On the one hand, upward growth and the development of a too luxuriant (and thus particularly frost-susceptible) leaf or plant mass are inhibited; on the other, the young rape plants are kept, in spite of favorable growth conditions, in the vegetative development stage before winter frosts begin. The danger of freeze injury is thus eliminated in plants which tend to lose prematurely their inhibition to bloom and pass into the generative phase. In other crops, too, e.g., winter cereals, it is advantageous if the plants are well tillered in the fall as a result of treatment with the compounds according to the invention, but enter winter with not too lush a growth. This is a preventive measure against increased susceptibility to freeze injury and—because of the relatively low leaf or plant mass—attack by various (especially fungus) diseases. The inhibition of vegetative growth also makes closer planting possible in numerous crops, which means an increase in yield, based on the area cropped.

B. Better yields both of plant parts and plant materials may be obtained with growth-regulating agents. It is thus for instance possible to induce increased formation of buds, blossom, leaves, fruit, seed grains, roots and tubers, to increase the sugar content of sugarbeets, sugarcane and citrus fruit, to raise the protein content of cereals and soybeans, and to stimulate the increased formation of latex in rubber trees.

The salicylic acid derivatives of the formula Ia may raise the yield by influencing plant metabolism or by promoting or inhibiting vegetative and/or generative plant growth.

C. It is also possible with growth regulators to shorten or lengthen growth stages and to accelerate or retard the ripening process in plant parts either before or after harvesting.

A factor of economic interest is for example the facilitation of harvesting made possible by a chemical, temporally concentrated loosening (abscission) of the adherence of stalks to the branches of citrus fruit, olive trees, and other kinds of pomes, drupes and indehiscent fruit. The same mechanism, i.e., promotion of the formation of separation layers between fruit or leaf and stem of the plant, is also essential for a readily controllable defoliation of crop plants, e.g., cotton.

D. Further, transpiration in crop plants may be reduced with growth regulators. This is particularly important for plants growing in agricultural areas which are expensive to irrigate, e.g., in arid or semi-arid areas. Irrigation frequency can be reduced by using the compounds according to the invention, making for lower costs. As a result of the use of growth regulators, the water available can be better utilized, because, inter alia,
the size of the stomata opening is reduced;
a thicker epidermis and cuticle are formed;
penetration of the soil by the roots is improved;
the micro-climate in the stand is favorably influenced by the more compact growth.

The active ingredients of the formula Ia to be used in accordance with the invention may be applied not only to the seed (as a disinfectant), but also to the soil, i.e., via the roots, and—the method particularly preferred—to the foliage by spraying.

As a result of the good crop plant tolerance, the application rate may vary considerably. When seed is treated, active ingredient amounts of from 0.001 to 50, and preferably from 0.01 to 10, g per kg of seed are generally needed. When the soil or foliage is treated, rates of from 0.001 to 10, and preferably from 0.01 to 3, kg per hectare are generally considered to be sufficient.

In view of the number of application methods possible, the herbicidal and growth-regulating agents according to the invention, or agents containing them, may be used in a further large number of crops for removing unwanted plants. The following crops are given by way of example:

| Botanical name | Common name |
| --- | --- |
| *Allium cepa* | onions |
| *Ananas comosus* | pineapples |
| *Arachis hypogaea* | peanuts (groundnuts) |
| *Asparagus officinalis* | asparagus |
| *Avena sativa* | oats |
| *Beta vulgaris* spp. altissima | sugarbeets |
| *Beta vulgaris* spp. rapa | fodder beets |
| *Beta vulgaris* spp. esculenta | table beets, red beets |
| *Brassica napus* var. napus | rapeseed |
| *Brassica napus* var. napobrassica | swedes |
| *Brassica napus* var. rapa | turnips |
| *Brassica rapa* var. silvestris | |
| *Camellia sinensis* | tea plants |
| *Carthamus tinctorius* | safflower |
| *Carya illinoinensis* | pecan trees |
| *Citrus limon* | lemons |
| *Citrus maxima* | grapefruits |
| *Citrus reticulata* | mandarins |
| *Citrus sinensis* | orange trees |
| *Coffea arabica* (*Coffea canephora, Coffea liberica*) | coffee plants |
| *Cucumis melo* | melons |
| *Cucumis sativus* | cucumbers |
| *Cynodon dactylon* | Bermudagrass |
| *Daucus carota* | carrots |
| *Elais guineensis* | oil palms |
| *Fragaria vesca* | strawberries |
| *Glycine max* | soybeans |
| *Gossypium hirsutum* (*Gossypium arboreum, Gossypium herbaceum, Gossypium vitifolium*) | cotton |
| *Helianthus annuus* | sunflowers |
| *Helianthus tuberosus* | Jerusalem artichoke |
| *Hevea brasiliensis* | rubber plants |
| *Hordeum vulgare* | barley |
| *Humulus lupulus* | hops |
| *Ipomoea batatas* | sweet potatoes |
| *Juglans regia* | walnut trees |
| *Lactuca sativa* | lettuce |
| *Lens culinaris* | lentils |
| *Linum usitatissimum* | flax |
| *Lycopersicon lycopersicum* | tomatoes |
| *Malus* spp. | apple trees |
| *Manihot esculenta* | cassava |
| *Medicago sativa* | alfalfa (lucerne) |
| *Mentha piperita* | peppermint |
| *Musa* spp. | banana plants |
| *Nicotiana tabacum* (*N. rustica*) | tobacco |
| *Olea europaea* | olive trees |
| *Oryza sativa* | rice |
| *Panicum miliaceum* | millet |
| *Phaseolus lunatus* | limabeans |
| *Phaseolus mungo* | mungbeans |
| *Phaseolus vulgaris* | snapbeans, green beans, dry beans |
| *Pennisetum glaucum* | pearl millet |
| *Petroselinum crispum* spp. tuberosum | parsley |
| *Picea abies* | Norway spruce |
| *Abies alba* | fir trees |
| *Pinus* spp. | pine trees |

| Botanical name | Common name |
|---|---|
| Pisum sativum | English peas |
| Prunus avium | cherry trees |
| Prunus domestica | plum trees |
| Prunus dulcis | almond trees |
| Prunus persica | peach trees |
| Pyrus communis | pear trees |
| Ribes sylvestre | redcurrants |
| Ribes uva-crispa | gooseberries |
| Ricinus communis | castor-oil plants |
| Saccharum officinarum | sugar cane |
| Secale cereale | rye |
| Sesamum indicum | sesame |
| Solanum tuberosum | Irish potatoes |
| Sorghum bicolor (s. vulgare) | sorghum |
| Sorghum dochna | sorgo |
| Spinacia oleracea | spinach |
| Theobroma cacao | cacao plants |
| Trifolium pratense | red clover |
| Triticum aestivum | wheat |
| Triticum durum | durum wheat |
| Vaccinium corymbosum | blueberries |
| Vaccinium vitis-idaea | cranberries |
| Vicia faba | tick beans |
| Vigna sinensis (V. unguiculata) | cow peas |
| Vitis vinifera | grapes |
| Zea mays | Indian corn, sweet corn, maize |

To increase the spectrum of action and to achieve synergistic effects, the compounds I and Ia according to the invention may be mixed and applied together with numerous representatives of other herbicidal or growth-regulating active ingredient groups. Examples of suitable components are diazines, 4H-3,1-benzoxazine derivatives, benzothiadiazinones, 2,6-dinitroanilines, N-phenylcarbamates, thiolcarbamates, halocarboxylic acids, triazines, amides, ureas, diphenyl ethers, triazinones, uracils, benzofuran derivatives, cyclohexane-1,3-dione derivatives, quinolinecarboxylic acid derivatives, aryloxy- or heteroaryloxy-phenoxypropionic acids and salts, esters and amides thereof, etc.

It may also be useful to apply the compounds I and Ia, either alone or in combination with other herbicides, in admixture with other crop protection agents, e.g., agents for combating pests or phytopathogenic fungi or bacteria. The compounds may also be mixed with solutions of mineral salts used to remedy nutritional or trace element deficiencies. Non-phytotoxic oils and oil concentrates may also be added.

SYNTHESIS EXAMPLES

The directions given in the synthesis examples below were used—after appropriate modification of the starting materials—to obtain further compounds I and Ia. The compounds thus obtained are listed with their physical data in the tables below. Compounds without any such data may be synthesized analogously from the appropriate starting materials. The structures given in the tables describe particularly preferred active ingredients of the formula I and Ia.

EXAMPLE 1

Manufacture of methyl-5-allyloxy-2-(4,6-dimethoxypyrimidin-2-yl)-oxy-benzoate 3.2 g of methyl-5-allyloxy-2-hydroxybenzoate in 10 ml of ethyl methyl ketone, and 20 g of potassium carbonate are added to 3.3 g of 4,6-di-methoxy-2-methylsulfonylpyrimidine in 70 ml of ethyl methyl ketone. The mixture is boiled for 4.5 hours, and then poured into ice water and extracted with methylene chloride. The extract is dried over sodium sulfate and evaporated down, and the oil which remains is purified by chromatography on silica gel. Melting point: 74°–75° C.

EXAMPLE 2

General directions for manufacturing substituted benzoic acids of the formula I 5.1 g of potassium hydroxide and 0.08 mol of the 2-hydroxybenzoic acid concerned are dissolved in 80 ml of methanol. The mixture is stirred at room temperature for 10 minutes and then concentrated under reduced pressure. Toluene is then repeatedly added for drying, followed by evaporation at 50° C. under reduced pressure. The light red powder thus obtained is taken up in 300 ml of dimethyl sulfoxide and 2.9 g of 80% strength sodium hydride is added in portions at room temperature. A gas evolves. When no more gas is liberated, a solution of 17.4 g of 4,6-dimethoxy-2-methylsulfonyl-pyrimidine in 80 ml of dimethyl sulfoxide is dripped in and the whole is stirred for 30 minutes. It is then poured into 2 liters of water, and the mixture is neutralized with acetic acid and washed with methylene chloride. The mixture is then strongly acidified with hydrochloric acid and extracted several times with methyl tert-butyl ether. The combined extracts are dried over sodium sulfate and the solvent is evaporated under reduced pressure. The remaining substance can be purified by chromatography on silica gel.

EXAMPLE 3

General directions for the manufacture of substituted benzoic acid oxime esters or similar compounds 3.2 mmol of the 2-(4,6-dimethoxypyrimidin-2-yl)-oxybenzoic acid concerned and 20 ml of dimethoxyethane are introduced into a receiver. 3.2 mmol of sodium hydride is added, a gas evolving immediately. The mixture is stirred for one hour at room temperature and cooled to 0° C., and 3.5 mmol of oxalyl chloride is added. The resulting mixture is stirred for one hour at 0° C., and about 30% of the solvent is evaporated under reduced pressure to remove the excess oxalyl chloride. 4.2 mmol of the oxime concerned, or a comparable hydroxy compound, dissolved in 10 ml of dimethoxyethane, and then 3.2 mmol of pyridine are added at 0° C., and the mixture is heated to room temperature over a period of one hour. The mixture is poured into 120 ml of cold water and extracted with methylene chloride, and the extract is dried over sodium sulfate and evaporated. The remaining substance can be purified further by chromatography on silica gel.

EXAMPLE 4

Manufacture of 2-chloro-6-(4,6-dimethoxytriazin-2-yloxy)-benzoic acid

At 25° C., 20.2 g of potassium tert-butylate is added in portions to 15.5 g of 2-chloro-6-hydroxybenzoic acid in 50 ml of dimethylformamide. Subsequently, 15.7 g of 2-chloro-4,6-dimethoxytriazine is added. The mixture is stirred for 12 hours at 25° C. and poured into cold water, and the resulting mixture is acidified with hydrochloric acid. Extraction is then carried out with ethyl acetate, and the extract is dried over sodium sulfate and the solvent is removed under reduced pressure. The residue is stirred with a small amount of diethyl ether, followed by filtration. The residue is dried under reduced pressure (m.p. 128°–131° C.).

TABLE 1

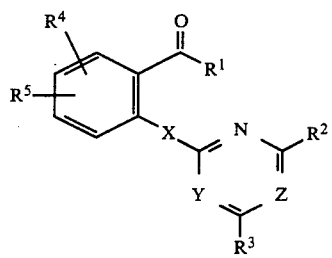

| No. | R¹ | R² | R³ | R⁴ | R⁵ | X | Y | Z | Phys. data |
|---|---|---|---|---|---|---|---|---|---|
| 1.001 | 2-propaneiminoxy | OCH₃ | OCH₃ | 6-Cl | H | O | N | CH | mp. = 92–94° C. |
| 1.002 | cyclohexaneiminoxy | OCH₃ | OCH₃ | 6-Cl | H | O | N | CH | δ = 2.40(m); 3.80 (s); 5.75(s) |
| 1.003 | cyclopentaneiminoxy | OCH₃ | OCH₃ | 6-Cl | H | O | N | CH | |
| 1.004 | 1-phenylethane-1-iminoxy | OCH₃ | OCH₃ | 6-Cl | H | O | N | CH | |
| 1.005 | succinyliminoxy | OCH₃ | OCH₃ | 6-Cl | H | O | N | CH | |
| 1.006 | 1-imidazolyl | OCH₃ | OCH₃ | 6-Cl | H | O | N | CH | mp. = 87° C. |
| 1.007 | OCH₃ | OCH₃ | OCH₃ | 6-Cl | H | S | N | CH | |
| 1.008 | OH | OCH₃ | OCH₃ | 6-Cl | H | S | N | CH | mp. = 156–159° C. |
| 1.009 | OH | OCH₃ | OCH₃ | 6-Cl | H | S | N | N | |
| 1.010 | OH | CF₃ | OCH₃ | 6-Cl | H | S | N | CH | |
| 1.011 | OCH₃ | OCH₃ | OCH₃ | 3-allyl | 6-Cl | O | N | CH | δ = 3.28(d); 3.75(s); 3.80(s); 5.05(m) |
| 1.012 | OH | OCH₃ | OCH₃ | 3-allyl | 6-Cl | O | N | CH | |
| 1.013 | OCH₃ | OCH₃ | OCH₃ | 3-(2-methylallyl) | 6-Cl | O | N | CH | |
| 1.014 | n-decanoxy | OCH₃ | OCH₃ | 6-Cl | H | S | N | CH | |
| 1.015 | 2-chloroallyloxy | OCH₃ | OCH₃ | 6-Cl | H | O | N | CH | |
| 1.016 | 2-propaneiminoxy | OCHF₂ | CH₃ | 6-Cl | H | O | N | CH | |
| 1.017 | 2-butaneiminoxy | OCH₃ | OCH₃ | 6-Cl | H | S | N | CH | |
| 1.018 | benzyloxy | CH₃ | CH₃ | 5-Cl | H | S | N | CH | |
| 1.019 | 3-chlorobenzyloxy | OCH₃ | OCH₃ | 5-Cl | H | S | N | CH | |
| 1.020 | OH | OCH₃ | OCH₃ | 6-Cl | H | O | CH | N | |
| 1.021 | OH | OCH₃ | CF₃ | 6-Cl | H | O | CH | CH | |
| 1.022 | OH | OCH₃ | CF₃ | 6-Cl | H | S | CH | CH | |
| 1.023 | 2-propaneiminoxy | OCH₃ | OCH₃ | 3-Cl | 5-Cl | O | N | CH | |
| 1.024 | 2-methylcyclohexaneiminoxy | OCH₃ | OCH₃ | 6-Cl | H | O | N | CH | |
| 1.025 | 3-dodecaneiminoxy | OCH₃ | OCH₃ | 6-Cl | H | O | N | CH | δ = 0.88(t); 1.08(t); 3.80(s); 5.75(s) |
| 1.026 | 2-methylhexane-3-iminoxy | OCH₃ | OCH₃ | 5-Br | H | O | N | CH | |
| 1.027 | 1-imidazolyl | OCH₃ | OCH₃ | 6-ethoxy | H | O | N | CH | |
| 1.028 | 2-propaneiminoxy | OCH₃ | OCH₃ | 6-F | H | O | N | CH | |
| 1.029 | ONa | OCH₃ | OCH₃ | 6-Cl | H | S | N | CH | |
| 1.030 | methylthiomethoxy | OCH₃ | OCH₃ | 6-Cl | H | S | N | CH | mp. = 90° C. |
| 1.031 | OCH₃ | OCH₃ | OCH₃ | 3-(2-chloroallyl | 6-Cl | O | N | CH | δ = 3.60(s); 3.75(s); 3.80(s); 5.75(s) |
| 1.032 | 1-([1,2,4]-triazolyl) | OCH₃ | OCH₃ | 6-Cl | H | O | N | CH | |
| 1.033 | OH | CF₃ | OCH₃ | 6-Cl | H | O | N | CH | |
| 1.034 | OH | OCH₃ | CH₃ | 6-Cl | H | S | N | CH | |
| 1.035 | 2-propaneiminoxy | OCH₃ | CH₃ | 6-Cl | H | O | N | CH | |
| 1.036 | 2-propaneiminoxy | OCH₃ | OCH₃ | 6-F | H | O | N | N | |
| 1.037 | cyclohexaneiminoxy | OCH₃ | OCH₃ | 6-F | H | O | N | CH | |
| 1.038 | OCH₃ | OCH₃ | OCH₃ | 3-allyl | 4-OH | O | N | CH | m.p. = 88–89° C. |
| 1.039 | OC₂H₄SC₂H₅ | OCH₃ | OCH₃ | 6-Cl | H | S | N | CH | δ = 1.20(t); 3.70(s); 4.43(t); 5.73(s) |
| 1.040 | OCH₂C≡CH | OCH₃ | OCH₃ | 6-Cl | H | S | N | CH | m.p. = 96–98° C. |
| 1.041 | 1-imidazolyl | OCH₃ | OCH₃ | 6-Cl | H | S | N | CH | m.p. = 102–103° C. |
| 1.042 | 2-methylhexane-3-iminoxy | OCH₃ | OCH₃ | 6-Cl | H | S | N | CH | δ = 1.13(d); 3.80(s); 5.75(s) |

*mp.: melting point
n_D: refractive index
δ: ¹H-NMR - chemical shift in ppm (selected signals).

TABLE 2

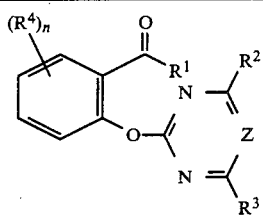

Ia

| Ex. | R¹ | R² | R³ | (R⁴)ₙ | Z | Phys. data |
|---|---|---|---|---|---|---|
| 2.001 | O—N=C(CH₃)CH₃ | OCH₃ | OCH₃ | 6-Cl | CH | 92–94 |
| 2.002 | O—N=cyclohexyl | OCH₃ | OCH₃ | 6-Cl | CH | |
| 2.003 | O—N=cyclopentyl | OCH₃ | OCH₃ | 6-Cl | CH | |
| 2.004 | O—N=C(C₆H₅)CH₃ | OCH₃ | OCH₃ | 6-Cl | CH | |
| 2.007 | pyrazolyl | OCH₃ | OCH₃ | 6-Cl | CH | 87 |
| 2.008 | OCH₃ | OCH₃ | OCH₃ | 6-CH₃ | N | 83–85 |
| 2.009 | OH | OCH₃ | OCH₃ | 6-Cl | N | 128–131 |
| 2.010 | OCH₃ | OCH₃ | OCH₃ | 6-Cl | N | 71–74 |
| 2.011 | OCH₃ | SCH₃ | SCH₃ | 6-Cl | N | 89–90 |
| 2.012 | OH | OCH₃ | OCH₃ | 5-OCH₂CH=CH₂ | CH | 143–145 |
| 2.013 | OCH₃ | OCH₃ | OCH₃ | 5-OCH₂CH=CH₂ | CH | 74–75 |
| 2.014 | OCH₃ | OCH₃ | OCH₃ | 6-OCH₂CH=CH₂ | CH | 84–85 |
| 2.015 | OCH₃ | OCH₃ | OCH₃ | 6-O—CH₂CH₂OCH₃ | CH | 83–85 |
| 2.016 | OCH₃ | OCH₃ | OCH₃ | 5-OCH₂CH=CH₂ | N | |
| 2.017 | OCH₃ | SCH₃ | OCH₃ | 5-OCH₂CH=CH₂ | N | |
| 2.018 | OCH₃ | OCH₃ | OCH₃ | 3-CH₂CH=CH₂, 6-Cl | CH | |
| 2.019 | OH | OCH₃ | OCH₃ | 3-CH₂CH=CH₂, 6-Cl | CH | |
| 2.020 | OCH₃ | OCH₃ | OCH₃ | 3-CH₂C(CH₃)=CH₂, 6-Cl | CH | |
| 2.021 | OCH₂C₆H₅ | OCH₃ | OCH₃ | 5-OCH₂CH=CH₂ | CH | |
| 2.022 | OCH₂COC₂H₅ | OCH₃ | OCH₃ | 6-Cl | CH | |
| 2.023 | O—N=C(CH₃)CH₃ | OCH₃ | OCH₃ | 5-OCH₂CH=CH₂ | CH | |
| 2.024 | OCH₂CH=CH₂ | OCH₃ | OCH₃ | 6-Cl | CH | |
| 2.025 | O—N=C(CH₃)CH₃ | OCHF₂ | CH₃ | 6-Cl | CH | |
| 2.026 | OH | OCH₃ | SCH₃ | 6-Cl | N | |
| 2.027 | OCH₂C≡CH | OCH₃ | OCH₃ | 6-Cl | CH | |
| 2.028 | OCH₂C≡CH | OCH₃ | OCH₃ | 5-OCH₂CH=CH₂ | CH | |

TABLE 2-continued

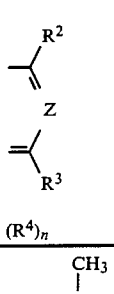

| Ex. | R¹ | R² | R³ | (R⁴)ₙ | Z | Phys. data |
|---|---|---|---|---|---|---|
| 2.029 | OCH₃ | OCH₃ | OCH₃ | 5-OCH₂C(CH₃)=CH₂ | CH | |
| 2.030 | OCH₃ | OCH₃ | OCH₃ | 5-OCH₂C(Cl)=CH₂ | CH | |
| 2.031 | 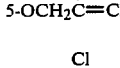 O—N=C(CH₃)₂ | OCH₃ | OCH₃ | 3-Cl, 5-Cl | CH | |
| 2.032 | 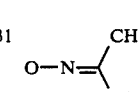 O—N=cyclohexyl | OCH₃ | OCH₃ | 5-OCH₂CH=CH₂ | CH | |
| 2.033 | 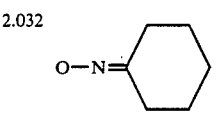 O—N=(2-methylcyclohexyl) | OCH₃ | OCH₃ | 6-Cl | CH | |
| 2.034 | O—N=C(C₂H₅)(C₉H₁₉) | OCH₃ | OCH₃ | 6-Cl | CH | |
| 2.035 | O—N=C(n-C₃H₇)(i-C₃H₇) | OCH₃ | OCH₃ | 5-Br | CH | |
| 2.036 | O-i-C₃H₇ | OCH₃ | OCH₃ | 6-OCH₂CH=CH₂ | CH | |
| 2.037 | 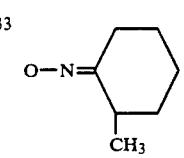 imidazolyl | OCH₃ | OCH₃ | 6-OC₂H₅ | CH | |
| 2.038 | O—N=C(CH₃)₂ | OCH₃ | OCH₃ | 6-F | CH | |
| 2.039 | 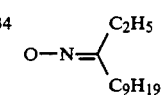 OCH₂-C₆H₄-OCH₃ | OCH₃ | OCH₃ | 4-CH₃ | N | |
| 2.040 | OCH₂OC₂H₅ | OCH₃ | OCH₃ | 6-Cl | N | |
| 2.041 | OH | OCH₃ | OCH₃ | 6-F | N | |
| 2.042 | OCH₂C(O)CH₃ | OCH₃ | OCH₃ | 6-Cl | N | |
| 2.043 | OCH₃ | OCH₃ | OCH₃ | 3-CH₂C(Cl)=CH₂, 6-Cl | CH | δ = 3.60(s); 3.75(s); 3.80(s); 5.75(s) |

TABLE 2-continued

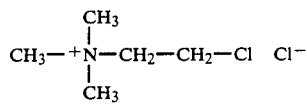

| Ex. | R¹ | R² | R³ | (R⁴)$_n$ | Z | Phys. data |
|---|---|---|---|---|---|---|
| 2.044 | O—N=C(CH₃)(CH₃) | OCH₃ | OCH₃ | 6-Cl | N | |

*mp.: melting point in °C.
$n_D$: refractive index
δ: ¹H-NMR - chemical shift in ppm (selected signals), measured in CDCl₃.

USE EXAMPLES DEMONSTRATING HERBICIDAL ACTION

The herbicidal action of the compounds of the formula I is demonstrated by the following greenhouse experiments:

The vessels employed were plastic flowerpots having a volume of 300 cm³ and filled with a sandy loam containing about 3.0% humus. The seeds of the test plants were sown separately, according to species.

In the preemergence treatment, the formulated active ingredients were applied to the surface of the soil immediately after the seeds had been sown. The compounds were emulsified or suspended in water as vehicle, and sprayed through finely distributing nozzles. The application rate was 0.03 kg of active ingredient per hectare. After the agents had been applied, the vessels were lightly sprinkler-irrigated to induce germination and growth. Transparent plastic covers were then placed on the vessels until the plants had taken root. The cover ensured uniform germination of the plants, insofar as this was not impaired by the active ingredients.

In the postemergence treatment, the plants were grown, depending on growth form, to a height of 3 to 15 cm before being treated. In this treatment method, either plants which had been sown in the pots and grown there were selected, or they were cultivated separately as seedlings and transplanted to the pots a few days before being treated. The application rates for postemergence treatment were 0.03 and 0.06 kg/ha. No covers were placed on the vessels in this method.

The pots were set up in the greenhouse, species from warmer climates in warmer areas (20° to 35° C.) and species from moderate climates at 10° to 25° C. The experiments were run for from 2 to 4 weeks. During this time the plants were tended and their reactions to the various treatments assessed. The assessment scale was 0 to 100, 100 denoting nonemergence or complete destruction of at least the visible plant parts, and 0 denoting no damage or normal growth.

The plants used in the greenhouse experiments were Abutilon theophrasti, Bromus inermis, Chenopodium album, Echinochloa crus-galli, Galium aparine, Lamium amplexicaule, Nicandra physaloides, Setaria italica and Solanum nigrum.

The compounds of Examples 1.001 and 1.002, applied pre- or postemergence at rates of 0.03 and 0.06 kg/ha, combated unwanted grasses and broadleaved unwanted plants very well. Use examples demonstrating growth-regulating action For comparison purposes, 2-chloroethyltrimethylammonium chloride (CCC; "A") was used:

$$CH_3-\overset{+}{\underset{CH_3}{\underset{|}{N}}}-CH_2-CH_2-Cl \quad Cl^-$$
$$\overset{|}{CH_3}$$

EXAMPLE I

Investigation of the growth-regulating action in cell suspensions of Indian corn (Grossmann and Jung, 1984, Plant Cell Rep., 3, 156-158)

2 ml suspensions were cultivated in sterile plastic test tubes. The candidate compounds were dissolved in acetone and added to the culture in a concentration of $10^{-4}$ mol.$1^{-1}$. After 8 days' incubation the conductivity of the culture medium was determined as a growth parameter, and the inhibition of growth in % was set against the control (0=no inhibition, 100=total growth inhibition).

The results show that, in the test system with cell suspensions, the agents according to the invention with compounds 2.009, 2.012, 2.013, 2.018 and 2.043 as active ingredients effectively inhibited cell growth (66 to 93% inhibition), and are far superior to comparative agent A (14% inhibition).

EXAMPLE II

Investigation of the growth-regulating action in a test system with duckweed (Lemna paucicostata)

The plants were grown photomixotrophically (addition of 1% of saccharose in an inorganic nutrient medium) under sterile conditions in permanent light. The candidate substances were dissolved in acetone and added to the duckweed at rates of $10^{-4}$ to $10^{-8}$ mol/-liter. After 8 days the increase in green weight of the plants was determined and the growth-regulating action of the compounds was calculated as a percentage inhibition of the growth of the control plants (0=no inhibition, 100=complete growth inhibition).

The results show that the agents according to the invention with compounds 2.009, 2.012, 2.013, 2.014, 2.015 and 2.018 as active ingredients in the test system inhibit duckweed growth to a significantly greater extent than comparative compound A. For example, at a molar concentration of $10^{-4}$, growth inhibition was 89 to 96%, whereas comparative agent A only achieved 32% inhibition.

EXAMPLE III

To determine the growth-regulating properties of the candidate compounds, the test plants were grown in plastic pots (approx. 12.5 cm in diameter and having a volume of approx. 500 ml) in a substrate provided with sufficient nutrients.

The compounds were sprayed as aqueous formulations onto the plants (postemergence application). The growth-regulating action observed was confirmed at the end of the experiment by measuring the height of the plants. The figures obtained were compared with the growth height of the untreated plants.

The reduction in growth height was also accompanied by a deeper leaf coloration. The increased chlorophyll content is indicative of an increased rate of photosynthesis, making for bigger yields.

The results are given in Tables IIa, IIb and IIc.

TABLE IIa

Spring wheat, "Ralle" variety

| No. of chemical example | Conc. mg a.i./vessel* | Growth height rel. |
|---|---|---|
| untreated | — | 100 |
| A | 0.05 | 90.5 |
|  | 0.1 | 87.3 |
|  | 0.38 | 87.3 |
|  | 1.5 | 81.1 |
| 2.009 | 0.05 | 53.0 |
|  | 0.1 | 53.0 |
|  | 0.38 | 53.0 |
|  | 1.5 | 49.9 |
| 2.012 | 0.05 | 100.0 |
|  | 0.1 | 96.7 |
|  | 0.38 | 71.7 |
|  | 1.5 | 53.0 |
| 2.013 | 0.05 | 71.7 |
|  | 0.1 | 67.1 |
|  | 0.38 | 53.0 |
|  | 1.5 | 49.9 |

*active ingredient/vessel

TABLE IIb

Spring barley, "Aramir" variety

| No. of chem. example | Conc. mg a.i./vessel* | Growth height rel. |
|---|---|---|
| untreated | — | 100 |
| A | 0.05 | 94.9 |
|  | 0.1 | 94.9 |
|  | 0.38 | 94.9 |
|  | 1.5 | 94.9 |
| 2.009 | 0.05 | 72.0 |
|  | 0.1 | 72.0 |
|  | 0.38 | 49.1 |
|  | 1.5 | 45.8 |
| 2.012 | 0.05 | 100.0 |
|  | 0.1 | 99.8 |
|  | 0.38 | 94.9 |
|  | 1.5 | 62.2 |
| 2.013 | 0.05 | 91.6 |
|  | 0.1 | 88.3 |
|  | 0.38 | 75.3 |
|  | 1.5 | 49.1 |

TABLE IIc

Sunflowers, "Spanners Allzweck" variety

| No. of chem. example | Conc. mg a.i./vessel* | Growth height rel. |
|---|---|---|
| untreated | — | 100 |
| A | 0.38 | 93.0 |

TABLE IIc-continued

Sunflowers, "Spanners Allzweck" variety

| No. of chem. example | Conc. mg a.i./vessel* | Growth height rel. |
|---|---|---|
|  | 1.5 | 93.0 |
| 2.043 | 0.38 | 100 |
|  | 1.5 | 76.8 |

*active ingredient/vessel

We claim:

1. A salicyclic acid derivative and its sulfur analogs of the formula I

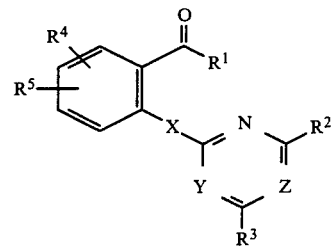

where the substituents have the following meanings:

$R^1$ is
1) a succinyliminooxy group;
2) a 5-membered heteroaromatic ring selected from the group consisting of imidazolyl, pyrazolyl and triazolyl which is unsubstituted or substituted by one to three halogen atoms and/or one or two of the following radicals: $C_1$-$C_4$-alkyl, $C_1$-$C_4$-haloalkyl, $C_1$-$C_4$-alkoxy, $C_1$-$C_4$-haloalkoxy and/or $C_1$-$C_4$-alkylthio;
3) a radical $ON=CR^7R^8$, where $R^7$ and $R^8$ are each $C_1$-$C_{20}$-alkyl which may carry a phenyl radical, or are each phenyl or together form a $C_3$-$C_{12}$-alkylene chain which may carry from one to three $C_1$-$C_3$-alkyl groups; or
4) a radical $-OR^6$, where $R^6$ is hydrogen, an alkali metal cation, one equivalent of an alkaline earth metal cation or an organic ammonium ion; $C_1$-$C_{10}$-alkyl which may carry from one to five halogen atoms and/or one of the following radicals: $C_1$-$C_4$alkoxy, $C_1$-$C_4$-alkylthio, cyano, $C_1$-$C_8$-alkylcarbonyl, $C_1$-$C_8$-alkoxycarbonyl, phenyl, phenoxy or phenylcarbonyl, where aromatic radicals in turn may carry from one to five halogen atoms and/or from one to three of the following radicals: $C_1$-$C_4$-alkyl, $C_1$-$C_4$-haloalkyl, $C_1$-$C_4$-alkoxy, $C_1$-$C_4$-haloalkoxy and/or $C_1$-$C_4$-alkylthio; or $C_3$-$C_6$-alkenyl or $C_3$-$C_6$-alkynyl, where these groups in turn may carry from one to five halogen atoms;

$R^2$ and $R^3$ are $C_1$-$C_4$-alkyl, $C_1$-$C_4$-haloalkyl, $C_1$-$C_4$-alkoxy, $C_1$-$C_4$-haloalkoxy and/or $C_1$-$C_4$-alkylthio;

X is oxygen or sulfur;

Y is nitrogen and

Z a methine group $=CH-$;

$R^4$ is halogen,
a $C_1$-$C_4$-alkyl or $C_1$-$C_4$-alkoxy group which may carry from one to five halogen atoms and/or one of the following radicals: $C_1$-$C_4$-alkoxy or $C_1$-$C_4$-alkylthio;
a $C_3$-$C_6$-alkenyl, $C_3$-$C_6$-alkenyloxy, $C_3$-$C_6$-alkynyl or $C_3$-$C_6$-alkynyloxy group which may carry from one to five halogen atoms and/or one of the following radicals: $C_1$-$C_4$-alkoxy or $C_1$-$C_4$-alkylthio;

$C_1$-$C_4$-alkylamino, $C_2$-$C_8$-dialkylamino, N-hydrogen-N-phenylamino or N-$C_1$-$C_4$-alkyl-N-phenylamino;

$R^5$ is hydrogen or one of the radicals $R^4$;

with the proviso that:
a) when $R^1$ is —$OR^6$ and X is oxygen, then
  i) $R^2$ is $C_1$-$C_4$-haloalkyl or
  ii) $R^4$ is $C_3$-$C_6$-alkenyl which may carry from one to five halogen atoms; or
b) when $R^1$ is —$OR^6$ and X is sulfur, then $R^6$ is $C_3$-$C_6$-alkenyl or $C_3$-$C_6$-alkynyl, where these groups in turn may carry from one to five halogen atoms; and their environmentally compatible salts.

2. A salicylic acid derivative of the formula I according to claim 1, wherein $R^1$ is $OR^6$ and $R^6$ is a propargyl group.

3. A process for combating the growth of unwanted plants, wherein the unwanted plants and/or their habitat are treated with a herbicidally effective amount of a derivative I as set forth in claim 1.

4. A process for regulating plant growth, wherein an amount sufficient for regulating plant growth of a salicylic acid derivative of the formula I as set forth in claim 1 is allowed to act on the seed, the plants and/or their habitat.

5. A sulfur analogs of a salicylic acid derivative of the formula Ia

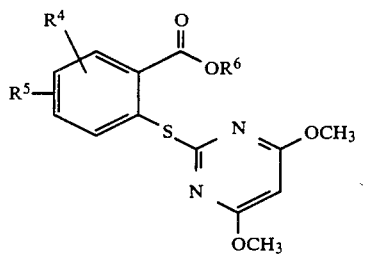

where the substituents have the following meanings:
$R^6$ is $C_3$-$C_6$-alkenyl or $C_3$-$C_6$-alkynyl, where these groups in turn may carry from one to five halogen atoms;
$R^4$ is halogen;
$R^5$ is hydrogen or halogen;
and their environmentally compatible salts.

6. A sulfur analog of a salicylic acid derivative of the formula Ia according to claim 5, wherein $R^6$ is a propargyl group, $R^4$ is halogen and $R^5$ is hydrogen.

7. The sulfur analog of a salicylic acid derivative of the following formula:

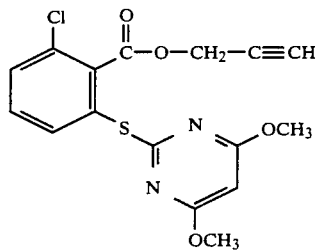

8. A salicylic acid derivative and its sulfur analog of the formula Ib

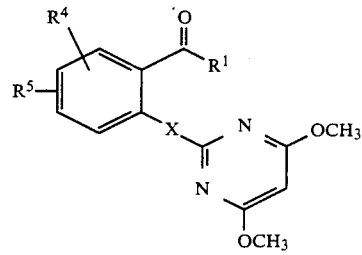

where the substituents have the following meanings:
$R^1$ is the group ON=$CR^7R^8$ where
$R^7$ and $R^8$ are each $C_1$-$C_{20}$-alkyl which may carry a phenyl group, or are each phenyl or together form a $C_3$-$C_{12}$-alkylene chain which may carry from one to three $C_1$-$C_3$-alkyl groups;
X is oxygen or sulfur;
$R^4$ is halogen;
$R^5$ is hydrogen or halogen;
and their environmentally compatible salts.

9. A salicylic acid derivative of the formula Ib according to claim 8 wherein $R^1$ is the group

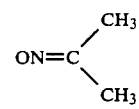

$R^4$ is halogen and $R^5$ is hydrogen.

10. The salicylic acid derivative of the formula

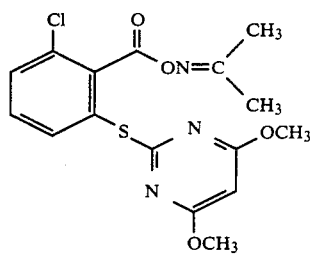

11. The salicylic acid derivative of the formula

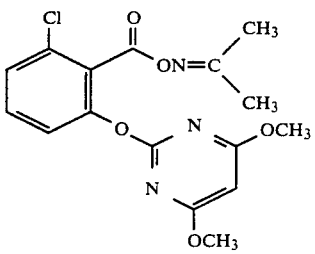

12. A salicylic acid derivative and its sulfur analog of the formula Ic

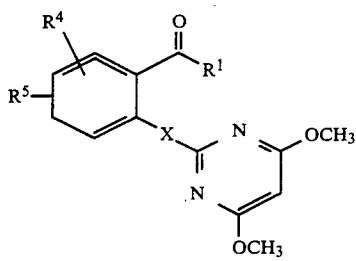

where the substituents have the following meanings:
R¹ is 1-imidazolyl group, which is unsubstituted or substituted by one to three halogen atoms and/or one or two of the following groups: $C_1$-$C_4$-alkyl, $C_1$-$C_4$-haloalkyl, $C_1$-$C_4$-alkoxy, $C_1$-$C_4$-haloalkoxy and/or $C_1$-$C_4$-alkylthio;
X is oxygen or sulfur;
R⁴ is halogen;
R⁵ is hydrogen or halogen;
and their environmentally compatible salts.

13. A salicylic acid derivatives of the formula Ic according to claim 12 wherein R¹ is an unsubstituted imidazolyl group, R⁴ is halogen and R⁵ is hydrogen or halogen.

14. A salicylic acid derivative of the formula

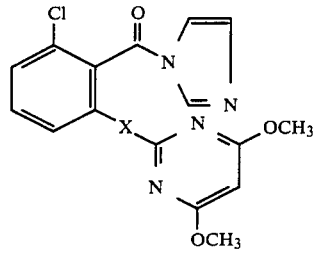

wherein X is oxygen or sulfur; and their environmentally compatible salts.

* * * * *

UNITED STATES PATENT AND TRADEMARK OFFICE
CERTIFICATE OF CORRECTION

PATENT NO. : 5,057,143

DATED : October 15, 1991

INVENTOR(S) : Joachim RHEINHEIMER et al.

It is certified that error appears in the above-identified patent and that said Letters Patent is hereby corrected as shown below:

Title Page:
In the Abstract, Line 4

"Salicyclic" should read --salicylic--

Claim 1, Column 26, line 11

"salicyclic" should read --salicylic--

Signed and Sealed this

Thirteenth Day of April, 1993

Attest:

STEPHEN G. KUNIN

Attesting Officer

Acting Commissioner of Patents and Trademarks